United States Patent [19]

Chang et al.

[11] Patent Number: 5,046,112
[45] Date of Patent: Sep. 3, 1991

[54] SUPPRESSION OF MACHINE MARKS ON IMAGE OF WORKPIECE SURFACE

[75] Inventors: Robert C. Chang, Murrysville; Nabeel W. H. Sufi, Franklin Township, Westmoreland County; Christopher W. Carroll, Pittsburgh, all of Pa.

[73] Assignee: Aluminum Company of America, Pittsburgh, Pa.

[21] Appl. No.: 442,522

[22] Filed: Nov. 28, 1989

[51] Int. Cl.⁵ ............................................. G06K 9/00
[52] U.S. Cl. ........................................ 382/8; 382/43
[58] Field of Search ............... 382/43, 31, 8; 364/726, 364/507

[56] References Cited

U.S. PATENT DOCUMENTS

| | | | |
|---|---|---|---|
| 4,223,345 | 9/1980 | Hannigan | 358/93 |
| 4,223,346 | 9/1980 | Neiheisel et al. | 358/106 |
| 4,240,110 | 12/1980 | Henry | 358/107 |
| 4,545,250 | 10/1985 | Miwa | 73/602 |
| 4,561,104 | 12/1985 | Martin | 382/8 |
| 4,633,504 | 12/1986 | Wihl | 382/54 |
| 4,637,055 | 1/1987 | Taylor | 382/31 |
| 4,741,621 | 5/1988 | Taft et al. | 356/376 |
| 4,817,176 | 3/1989 | Marshall et al. | 382/43 |
| 4,843,631 | 6/1989 | Steinpichler et al. | 382/43 |

OTHER PUBLICATIONS

Hecht, Eugene/Zajac, Alfred, "Optics", Adelphi University, copyright 1974, Addison-Wesley Publishing Company, Inc., p. 472.

Primary Examiner—Stephen Brinich
Attorney, Agent, or Firm—Elroy Strickland

[57] ABSTRACT

A method of inspecting the surface of an object for the detection and analysis of surface variations that exceed established acceptable surface conditions. The surface has a directionally specific pattern that tends to obscure surface variations in a spatial domain of the surface. The method includes detecting the presence of one or more surface variations with sensors located to view the surface and to provide an electronic image of an area of the surface containing said variations and directionally specific pattern. The electronic image is transmitted from the sensors to a storage device for subsequent display and analysis. The spatial domain of the image is transformed into a two dimensional frequency domain to obtain a spectral response of the image. Frequency components of the two dimensional spectral response are then evaluated to identify the direction of the directionally specific pattern. A band eliminating filter having a spectral response corresponding to said pattern is provided and used to remove or at least suppress the pattern from the stored image.

8 Claims, 5 Drawing Sheets

GENERATION OF AN APPROXIMATE FILTER KERNEL

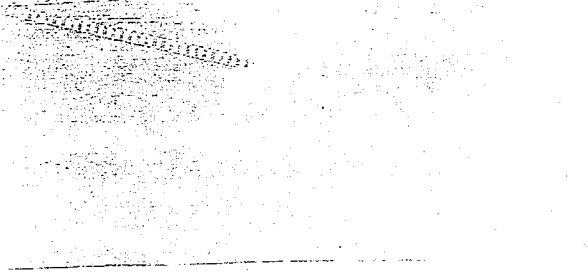

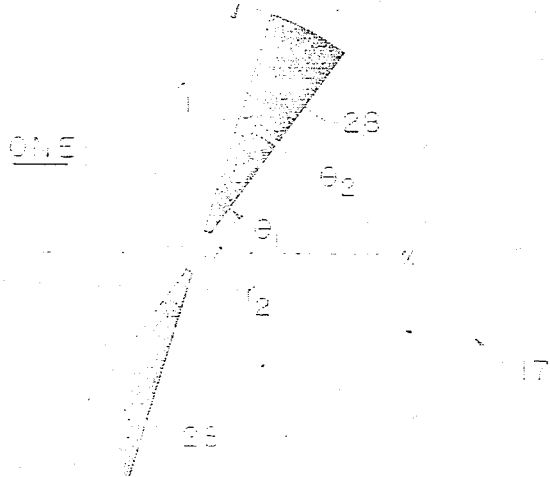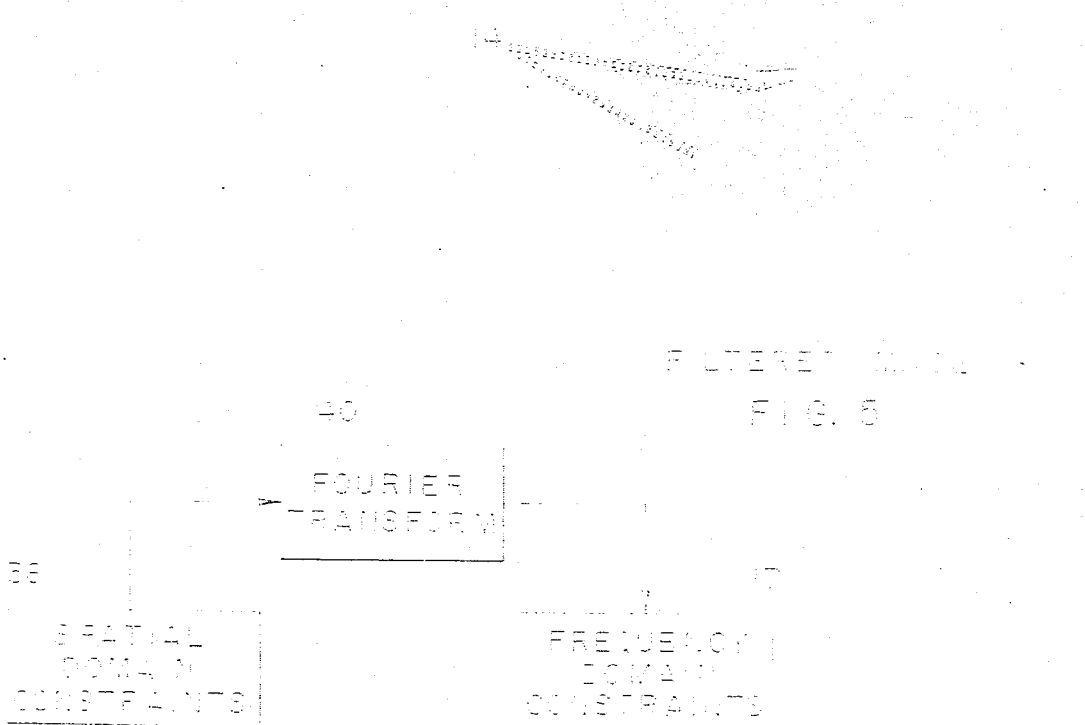

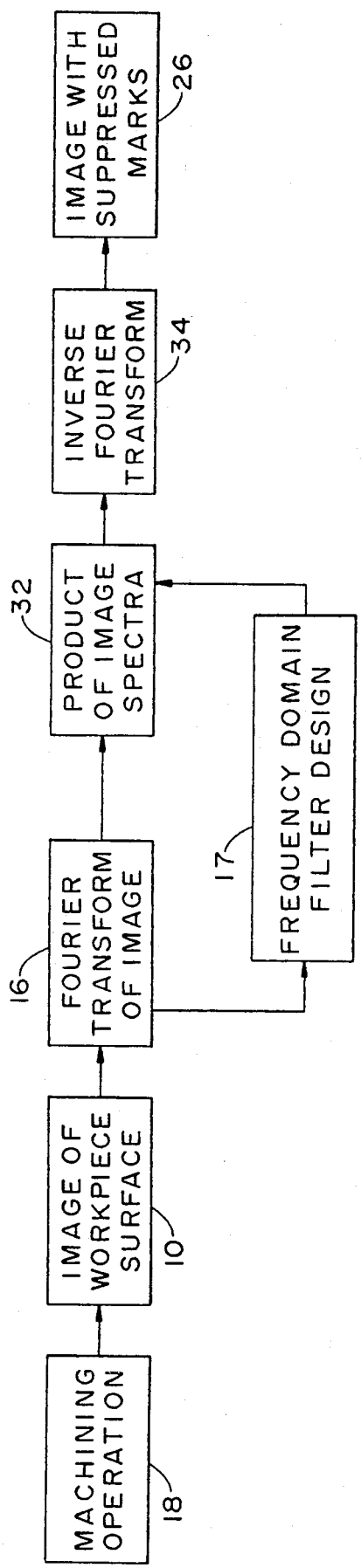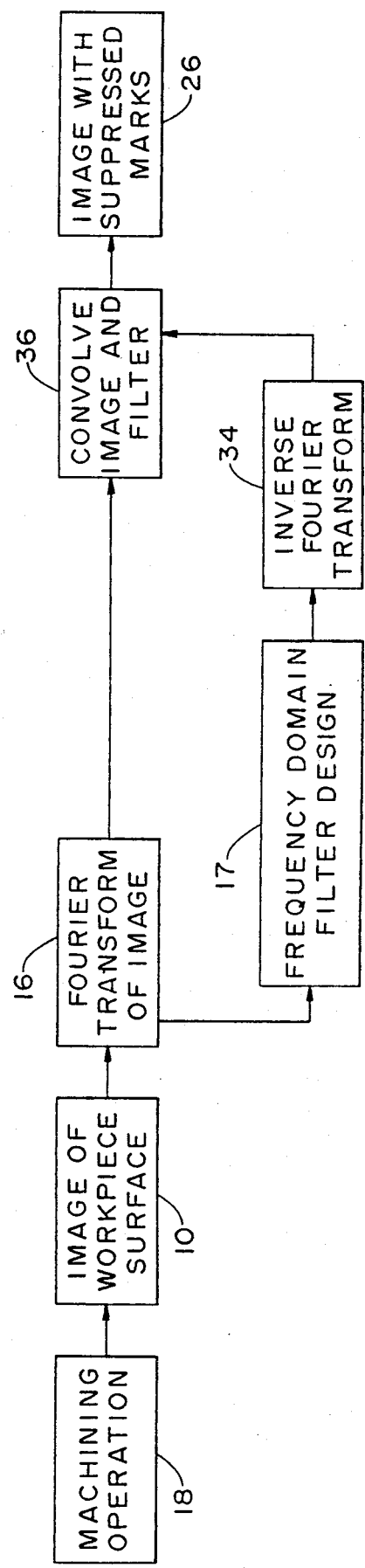
FIG. 6 — DIGITAL COMPUTING IMPLEMENTATION (FREQUENCY DOMAIN)
FIG. 7 — DIGITAL COMPUTING IMPLEMENTATION (SPATIAL DOMAIN)

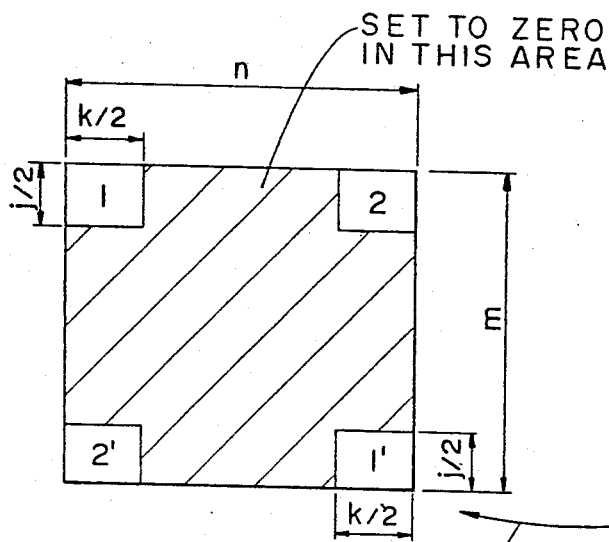
SPATIAL DOMAIN 38
FIG. 9a
n = m = 512 LINES
j = k = 13 LINES
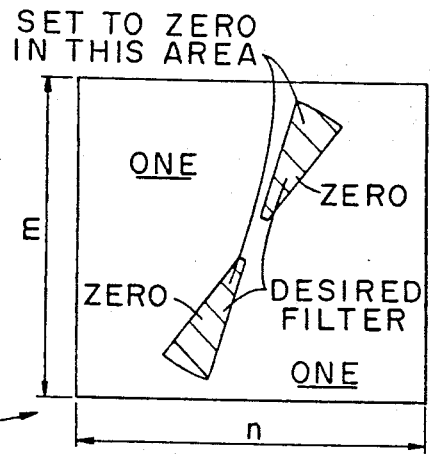
FREQUENCY DOMAIN 40
FIG. 9b
BACK AND FORTH BETWEEN FREQUENCY AND SPATIAL DOMAINS TO SET ZEROS UNTIL THE PROCESS CONVERGES, i.e. UNTIL SETTING TO ZERO IS NO LONGER NECESSARY
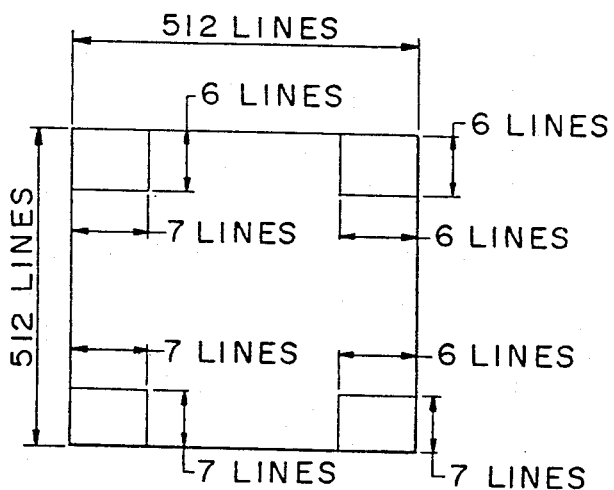
NUMERICAL EXAMPLE
FIG. 9c
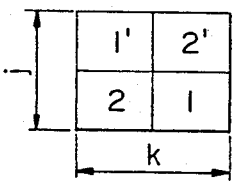
SMALL SIZE KERNEL
FIG. 9d
ERROR REDUCTION ALGORITHM
FIG. 9

OPTICAL COMPUTING IMPLEMENTATION

SUPPRESSION OF MACHINE MARKS ON IMAGE OF WORKPIECE SURFACE

BACKGROUND OF THE INVENTION

The present invention relates generally to visually inspecting surfaces, such as images of such surfaces acquired by a television camera, and more particularly to the suppression of directionally specific patterns on the acquired images in order to expose and better assess other surface features of interest. The features of interest may be flaws or defects on the surface of a moving or stationary workpiece, while the directionally repetitive pattern may be one created by machine marks of a tool that has prepared (machined) the surface in some manner.

Much technology exists and many patents have issued on techniques for inspecting moving and stationary surfaces, but none have dealt with the suppression of machine marks on the surface that extend in specific directions and obscure flaws and defects to the extent that detection and analysis of flaws cannot be adequately made. The reasons for this is that the machine marks themselves appear as defects and/or obscure the defects, particularly on an image of the surface containing defects as provided by a television camera and a cathode ray tube (television) monitor.

SUMMARY OF THE INVENTION

As discussed in detail hereinafter, the present invention is directed to suppressing (or removing altogether) directionally specific machine marks from an image, such as a television frame, of a surface under inspection so that any defects or flaws on the surface can be seen and analyzed. The flaws are analyzed so that the manufacturing process is not halted for minor and inconsequential flaws; more serious defects are identified for removal either by removing those portions of the product that have such defects or by scrapping the entire product, such as a coil of sheet metal.

The basic concept of the embodiments of the invention involves the transformation of the machine marks from a spatial domain, as they exist on the "space" (surface) of a workpiece, to a two dimensional frequency domain, such as provided by a fast Fourier transform, to obtain a spectral (frequency) response of the machine pattern. Based upon an evaluation of frequency components of the spectral response, the directional pattern can be identified. A filter, which matches the spectral content of the directional specific repetitive machine marks, is employed to remove or suppress the frequency) of the directional pattern. The frequency domain is then returned to the spatial domain so that an acquired image of the surface can be viewed without the interfering pattern, or with at least a reduced presentation of the pattern in the image so that flaws become more pronounced.

It is therefore a primary objective of the invention to filter out machine marks (that would otherwise appear in an electronic or optical image of a surface area containing the marks) while leaving any defects intact in the image. If one is too aggressive in removing machine marks, the defects will also be removed.

Another objective of the invention is to first determine the direction of the marks on the surface, and then apply a rotated version of the filter to the image so that the operation of the filter is not directionally limited. In the case of a circular pattern, as formed by a milling cutter, for example, the electronic image of the milled surface can be segmented such that only an arc of the circular pattern will appear, thereby approximating straight lines in the resulting sub-images. The amount of the above rotation of the filter is then determined for each sub-image. Spacing between the blade marks is not a problem due to the fact that the filter removes a broad range of spatial frequencies.

A further objective of the invention is to filter out semi-circular scalper blade marks on an ingot surface, as presented in an image of the surface, while leaving intact any surface flaws. Again, by segmenting a relatively large image area into several sub-images of the surface, the blade marks can be approximated as straight lines.

THE DRAWINGS

The objectives and advantages of the invention will be better understood by consideration of the following detailed description in connection with the accompanying drawings in which:

FIG. 1 is a video print of a digitized image (frame) of a surface of aluminum ingot scalped by scalper blades, the image having been developed using 512 column scans by 480 rows of a television frame (screen), with each pixel represented by eight bits in digitizing the analogue signal of the pixel.

FIG. 2 is an enlarged view of a video image and frame of a scalped ingot surface containing surface defects. FIG. 1 shows curved marks that, in FIG. 2, approximate straight lines because of the enlargement of the image;

Figure 10:
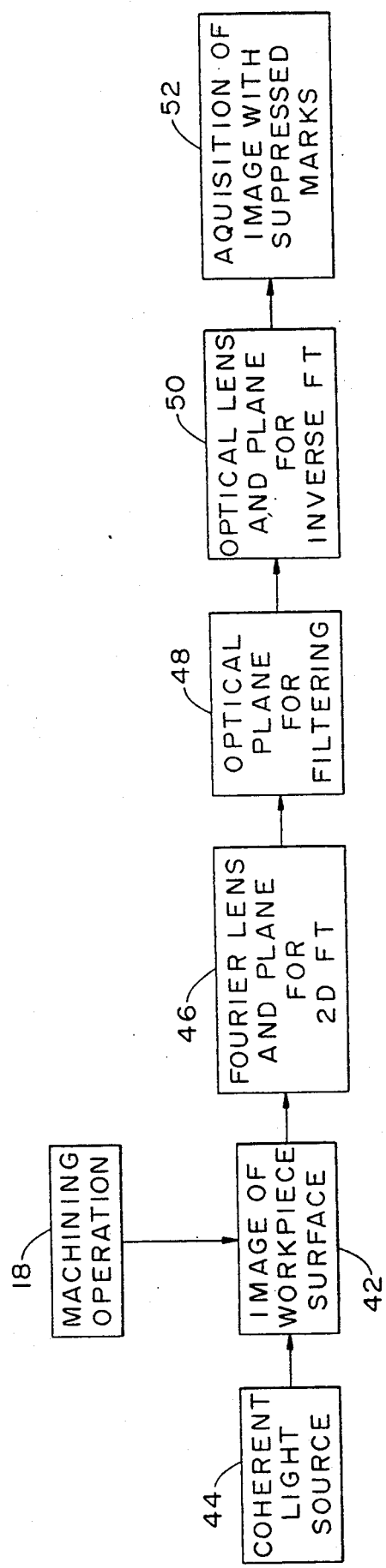

FIG. 3 is a two dimensional Fourier transform of the image of FIG. 2. The magnitude of the transformation displayed in FIG. 3 uses a base 10 logarithmic scale. The diagonal bright region in FIG. 3 corresponds to the blade mark information in FIG. 2 that requires suppression or removal from the image of the ingot surface;

FIG. 4 is a binary frequency domain filter mask employed in the above suppression or removal of the blade marks;

FIG. 5 shows the results of the filter mask of FIG. 4, i.e., the blade marks are removed from the image, and surface defects remain;

FIG. 6 is a block diagram depicting implementation of the invention in digital computing form, using a frequency domain filter;

FIG. 7 is a block diagram showing implementation using a digital convolution algorithm;

FIG. 8 is a flow diagram of an Error Reduction Algorithm for approximating a small size filter kernel;

FIGS. 9A-9D show the process of FIG. 8 in pictorial form, which is a convolution process that constrains an image kernel to a size smaller than the original, and FIG. 10 is a block diagram showing implementation of the invention using optical computing in the frequency domain.

PREFERRED EMBODIMENTS

Referring now to FIG. 1 of the drawings, a video image 10 of a scalped surface of an aluminum ingot is shown. The scalped surface, and the image of the surface, have repetitively occurring curved lines or marks 12 that tend to obscure surface flaws 14 (FIG. 2). The curved marks are caused by the blades (not shown) of a "scalper" that removes surface metal in the process of truing the ingot for breakdown. In the broad context of the invention marks 12 are representative of any marks formed on a surface by machining, said marks tending to obscure flaws on the machined surface.

FIG. 2 of the drawings shows an enlarged portion of an image such as the one depicted in FIG. 1 containing flaws 14. If machine marks 12 are removed from the image, as in FIG. 5 of the drawings, flaws 14 are more easily seen by personnel observing the image on a television screen.

Removal of machine marks 12 is accomplished by the use of a two dimensional Fourier transform 16 (FIG. 3) of the marks and a two dimensional frequency domain filter mask 17 (FIG. 4). The marks appear in the image 10 of the ingot surface, which image is in the spatial domain of the surface. The removal process is shown diagrammatically in FIG. 6. As shown, an image 10 (box 10) of a surface resulting from a machining operation at 18 is provided. The image can be provided by one or more sensors, such as television cameras (not shown) located to view the scalped surface, which image is then sent to the storage portion of a digital computer (represented in part in the drawings by Fourier transforms) for subsequent display and analysis at 26 (FIG. 6). The scalped surface is exposed to light, visible or invisible, to provide a surface viewable by the cameras. Storage device 22 includes the Fourier transform (box 16) of FIG. 3.

The image, before being sent to storage, is provided by the cameras and consists of analogue signals which are digitized in a well known manner to provide the image frames shown in FIGS. 1 and 2, and schematically represented at 10 in FIG. 6.

The transform of FIG. 3 produces bright portions 24 that correspond to the blade marks 12 in FIG. 2. It is the bright portions that need to be suppressed or removed from the image so that flaws 14 (FIG. 2) will be more visible for observation and analysis at 26 in FIG. 6. The transform is shifted in FIG. 3 so that the DC component thereof lies in the center of the frame.

The frequency domain provided by the transform 16 allows one to obtain a spectral response of the image acquired at 10 by the television cameras. Based upon an evaluation of the frequency response, the direction of the pattern 12 can be identified and the filter 17 of FIG. 4, spectrally responsive to the repetitive pattern of 12, and which thus matches the spectral content of the directionally specific machine marks, is designed, as explained below, and employed to remove or suppress the frequency of the pattern.

As shown in FIG. 4 of the drawings mask 17 has two opposed wings 28 that match the bright portions 24 of the transform 16 of FIG. 3. These wings are comprised of pixels of value zero while the remaining pixels in the field have a value of one, i.e., the wings depicted in FIG. 4 were digitally generated off-line, as shown in FIG. 6. The mask, for example, can be digitally contained on a computer disc or placed in the memory of the computer.

The filter 17 of FIG. 4 is a band eliminating device, i.e, the mask of FIG. 4 is one that eliminates the band of frequencies that are oriented with the machine marks 12 in FIGS. 1 and 2.

Only one mask 17 is necessary, as each frame, in the process of acquiring successive images of a machined surface, will be essentially the same since the machining tool repeats the pattern.

The filtering of blade marks 12 is now obtained at 32 (FIG. 6) by arithmetically multiplying the intensity of each pixel in the Fourier transform of the image 16 (FIG. 3) by the intensity of each pixel in the image of mask 17 (FIG. 4) in the computer. The result of the multiplication, i.e, the product 32, which is now a digitized image of a machined surface without marks 12, or with the marks severely suppressed in the image, is inversely fast Fourier transformed at 34 to return the image to the spatial domain. This image is shown in FIG. 5 of the drawings. The digital spatial image can now be converted to analog signals and displayed on a television monitor at 26 for viewing and analysis without the bothersome machine marks.

There are variations that can occur over a large set of image data that may effect the performance of filter 17. The main variations are 1) orientation of the machine marks, 2) the curvature of the machine marks, and 3) the spacing between the machine marks. The filter shown in FIG. 4 of the drawings is directionally specific and tolerates only a moderate deviation in the orientation of the original machine marks. Fortunately, it is possible to rotate or align the filter about its DC component in the frequency domain to allow a suppression of blade marks running in any arbitrary direction. It is therefore necessary to determine the direction of the blade marks before applying the filter, and then applying a version of the filter that is aligned with the blade mark of the image of FIG. 3. This can be accomplished by arithmetic operations in the computer. For example, a Euler transformation can be used to transfer filter pixel coordinates to a portion that aligns the wings 28 of mask 17 with the bright portions 24 of transform 16. However, a preferred way is to simply determine the filter parameters, which are the outer and inner radii $r_1$ and $r_2$ of wings 28 (see FIG. 4) and their angles $\theta_1$ and $\theta_2$ relative to the x axis of the wings, which provides the rotation of the wings, and forms the filter at the desired angle. Digitally, the intensity value of the pixels of the area inside of the wings can be zero while the intensity value of the area outside the wing area can be one.

The curvature of the marks is important when dealing with large area machined surfaces, such as a large scalped aluminum ingot, the surface of which is included in a single image. Such marks are actually circular patterns and thus complete removal of such patterns would result in severe attenuation of the defects. One method to minimize this is the segmentation of the large area image into several sub-images, where the blade marks will approximate straight lines. FIG. 2 is an example of this. The proper amount of the rotation of filter 17 is then determined for each sub-image.

As noted earlier, the space between the marks is not a substantial problem, as filter 17 removes a broad range of spatial frequencies.

FIG. 7 of the drawings shows an arrangement in which implementation of the invention can be accomplished in real-time by use of an algorithm that convolves the spatial image of a machined surface at 36 after the frequency domain filter 17 is designed and applied, and after the inverse Fourier transform 34 transforms the image of the filter. Because the same tool does the machining, the filter needs to be designed only once.

The processing performed in FIG. 7 uses a low-resolution approximation of the desired filter (17), i.e, approximation is accomplished by a filter that uses a small-size kernel convolution. In determining the size of the filter kernel a trade-off exists between the speed of the computer hardware and the resolution required to remove marks 12 while preserving defects 14 in the image.

The generation of an appropriate filter kernel at 36 can be accomplished by using an Error Reduction Algorithm. A block diagram of the method is shown in FIG. 8 of the drawings. An "image" diagram of the method is shown in FIG. 9. The application of the algorithm to the problem of suppressing machine marks begins by specifying a high resolution, binary mask in the frequency domain, as shown at 17 in FIGS. 7 and 8. The binary mask in the frequency domain is inversely transformed at 34 to the spatial domain at 38 in FIG. 8. Ordinarily, this results in a convolution kernel that is the size of the original image of the workpiece surface m x n, see FIG. 9a. FIG. 9a is the spatial domain constraint of 38 in FIG. 8, the constraint being accomplished by setting the large original kernel m×n to be non-zero over four smaller j/2×k/2 areas shown located respectively in the four corners of the original kernel, and setting the remaining area to zero, as shown and stated in FIG. 9. The new kernel, now comprised of j×k, depicted in the lower right box (FIG. 9d), which box comprises the four corner boxes of FIG. 9a, is transformed back into the frequency domain at 40 (FIGS. 8 and 9b); here, the pixels that correspond to zeros in the original filter mask are set to zero. This cycle continues until convergence of the image to the small size kernel (j×k) is reached and a small size filter approximation is obtained.

FIG. 9c provides a "numerical example" of the Error Reduction Algorithm of FIG. 8. The original size of the image is formed by the 512 scan lines of the normal television monitor. The constraint provided by the Algorithm provides the reduced size of j×k, using only thirteen lines, by employing box sizes defined by six and seven scans for each corner box. These boxes are labelled 1, 2, 1' and 2' in FIG. 9a, and, as explained above, are brought together by the Algorithm, and the computer, to form the small size j×k kernel of FIG. 9d.

Another method for obtaining real-time implementation of the invention involves the use of optical data processing. This method uses the Fourier transform properties of coherent light to perform the conversion into and out of the spatial frequency domain of the image of the machined surface. A simplified block diagram of such a system is shown in FIG. 10 of the drawings. A continuous, spatial image of the workpiece is provided at 42. A transparency or other two dimensional spatial light modulator can be used for this purpose. Coherent light (at 44) is directed through such an image, and to a Fourier lens and plane at 46, which performs a two dimensional Fourier transform of the spatial image. An optical filter 48, which corresponds to the video filter 17 in FIG. 4, is located in optical alignment with the Fourier lens and plane 46. The filter removes the blade marks from the optical image of the machined surface at 46. The frequency domain of the filtered image is now returned to the spatial domain by another Fourier transform lens at 50. A video camera 52 can now capture the spatial image provided by 50 to provide (display) an image of the surface having the machine marks 12 suppressed or eliminated from the captured image, as in FIG. 5 of the drawings.

While the invention has been described in terms of preferred embodiments, the claims appended hereto are intended to encompass all embodiments which fall within the spirit of the invention.

What is claimed is:

1. A method of inspecting the surface of an object for the detection and analysis of surface variations that exceed established acceptable surface conditions, said surface having at least one directionally specific pattern that tends to obscure said surface variations in a spatial domain, said method comprising:
   exposing a surface of the object to electromagnetic visible and/or invisible energy,
   detecting the presence of one or more surface variations with sensors located to view the surface and thereby acquire an electronic image of an area of the surface containing said variations and directionally specific pattern,
   transmitting said electronic image from one or more of the sensors to a device for storing said image for subsequent display and analysis,
   transforming the spatial domain of the acquired image into a two dimensional frequency domain to obtain a spectral response of the acquired image,
   evaluating frequency components of the two dimensional spectral response to identify the direction of the directionally specific pattern,
   providing a band eliminating filter having a spectral response that corresponds with said pattern, and
   using said filter to remove or at least suppress the pattern from the image stored for subsequent display and analysis.

2. The method of claim 1 including:
   designing a band eliminating filter based on the evaluation of frequency components of said spectral response to remove the directional pattern from the acquired image of the object surface.

3. The method of claim 1 including:
   using fast Fourier transformation to transform the spatial domain of the image to the frequency domain, and
   an inverse fast Fourier transformation to return said image to the spatial domain.

4. The method of claim 3 including:
   using a digital computer to (1) effect the Fourier transforms of the electronic image, (2) to evaluate the directional component in the spectral response, and (3) to filter said directional component.

5. The method of claim 3 including
   using optical means to (1) effect the Fourier transforms of the electronic image, (2) to evaluate the directional component in the spectral response, and (3) to filter said directional component.

6. The method of claim 1 including:
   convolving the spatial image with a spatial domain filter kernel obtained through the inverse Fourier transformation of the filter of claim 2.

7. The method of claim 6 in which the convolving step includes using a small-sized filter kernel obtained from an Error Reduction Algorithm.

8. The method of claim 7 including:
   obtaining from a high resolution binary mask in the frequency domain a convolution kernel that corresponds in size to the size of the acquired image in the spatial domain,
   reducing the size of the kernel by constraining it to a small, non-zero area of the spatial image,
   transforming the kernel to the frequency domain,
   applying zero constraints of the mask to said kernel, and
   continuing the cycle of transformations until convergence is reached and a small size filter approximation is obtained.

* * * * *